(12) United States Patent
Linge et al.

(10) Patent No.: US 9,308,240 B2
(45) Date of Patent: *Apr. 12, 2016

(54) METHOD OF PREVENTING OR REDUCING SCARRING OF HUMAN SKIN

(71) Applicant: Pharmecosse Limited, Dundee (GB)

(72) Inventors: Claire Linge, Harrow (GB); Ian Paul Mackie, Sheffield (GB)

(73) Assignee: Pharmecosse Limited, Dundee (GB)

( * ) Notice: Subject to any disclaimer, the term of this patent is extended or adjusted under 35 U.S.C. 154(b) by 12 days.

This patent is subject to a terminal disclaimer.

(21) Appl. No.: 14/025,809

(22) Filed: Sep. 12, 2013

(65) Prior Publication Data

US 2014/0155322 A1 Jun. 5, 2014

Related U.S. Application Data

(63) Continuation of application No. 11/960,327, filed on Dec. 19, 2007, now Pat. No. 8,557,770, which is a continuation of application No. 10/239,904, filed on Sep. 26, 2002, now abandoned, which is a continuation-in-part of application No. PCT/GB01/05273, filed on Nov. 29, 2001.

(30) Foreign Application Priority Data

Nov. 29, 2000 (GB) .................................. 0029138.5

(51) Int. Cl.
*A61K 38/28* (2006.01)
*A61K 45/06* (2006.01)

(52) U.S. Cl.
CPC ................ *A61K 38/28* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,861,757 A | 8/1989 | Antoniades et al. | |
| 4,876,242 A | 10/1989 | Applebaum et al. | |
| 4,885,163 A | 12/1989 | Shaar et al. | |
| 4,983,581 A | 1/1991 | Antoniades et al. | |
| 5,019,559 A | 5/1991 | Antoniades et al. | |
| 5,124,155 A | 6/1992 | Reich | |
| 5,256,644 A | 10/1993 | Antoniades et al. | |
| 5,324,820 A | 6/1994 | Baxter | |
| 5,461,030 A | 10/1995 | Lindenbaum | |
| 5,473,054 A | 12/1995 | Jameson et al. | |
| 5,561,046 A | 10/1996 | Baxter | |
| 5,591,709 A | 1/1997 | Lindenbaum | |
| 5,736,511 A | 4/1998 | Baxter | |
| 5,849,687 A | 12/1998 | Baxter | |
| 5,866,167 A | 2/1999 | Van Bossuyt | |
| 5,866,360 A | 2/1999 | Baxter | |
| 6,582,713 B2 | 6/2003 | Newell et al. | |
| 8,557,770 B2 | 10/2013 | Linge | |
| 2002/0122787 A1* | 9/2002 | Newell et al. | 424/78.37 |
| 2005/0054608 A1 | 3/2005 | Linge | |

FOREIGN PATENT DOCUMENTS

| | | |
|---|---|---|
| CA | 1 243 948 | 11/1988 |
| EP | 0 162 007 A1 | 11/1985 |
| EP | 0 280 460 A2 | 8/1988 |
| EP | 0 561 330 A1 | 5/1995 |
| JP | 1022254 | 1/1989 |
| JP | 5084290 | 4/1993 |
| JP | 10265405 | 10/1998 |
| WO | 88/03409 | 5/1988 |
| WO | 91/15231 | 10/1991 |
| WO | 91/18622 | 12/1991 |
| WO | 93/04691 | 3/1993 |
| WO | 93/10795 | 6/1993 |
| WO | 94/04030 | 3/1994 |
| WO | 94/20133 | 9/1994 |
| WO | 96/02270 A1 | 2/1996 |
| WO | 96/25943 | 8/1996 |
| WO | 99/11789 | 3/1999 |
| WO | 99/66797 | 12/1999 |
| WO | 99/66923 | 12/1999 |
| WO | 00/10610 | 3/2000 |
| WO | 00/33893 | 6/2000 |
| WO | 01/76650 | 10/2001 |
| WO | 02/087576 | 11/2002 |

OTHER PUBLICATIONS

Michalik et al, Impaired Skin Wound Healing in Peroxisome Proliferator-activated Receptor (PPAR) and PPAR Mutant Mice, The Journal of Cell Biology (2001), vol. 154, p. 799-814.
Lesion definition: http://216.251.232.159/semdweb/internetsomd/ASP/1533197.asp, 2005.
Symposion: Keloids and Hypertrophic Scars, Grand Round, Oct. 1999, see http://www.ulc.edu/depts/doms/rounds/rounds-35.html.
Presentation: Belfield et al in a paper presented by Dr. Belfield at the 81st Annual Convention of the California Veterinary Medical Association, Oct. 1969, see http://www.belfield.com/VM-SAC_05-70.pdf.
Greenway S.E. et al., "Topical Insulin in Wound Healing: A Randomized, double-blind, placebo-controlled Trial," Journal of Wound Care, vol. 8, No. 10, (1999), pp. 526-528.
http://www.drugs.com/pdr/lletin_ll.html Handout, 2005.

* cited by examiner

*Primary Examiner* — Thomas S Heard
(74) *Attorney, Agent, or Firm* — David A Chavous; David A Giordano; Giordano & Chavous LLC (57) ABSTRACT

Insulin or a peroxisome proliferator-activated receptor (PPAR) agonist provides reliable and effective prevention of scarring in human skin, or at least a reduction in the severity of scarring. The application of insulin or the PPAR agonist to wounds topically or by local injection is particularly advantageous since it simultaneously reduces/prevents scarring while enhancing re-epithelialization of the wound and thus provides a dual action wound healing treatment. The present invention accordingly provides a highly effective prophylactic treatment for any individual suffering tissue trauma to reduce and/or prevent normal and/or pathological scarring.

9 Claims, 3 Drawing Sheets

METHOD OF PREVENTING OR REDUCING SCARRING OF HUMAN SKIN

CROSS REFERENCE TO RELATED APPLICATION

This application is a continuation of Ser. No. 10/239,904, filed Nov. 26, 2002 which is a continuation-in-part of International Patent Application No. PCT/GB01/05273, filed Nov. 29, 2001.

FIELD OF THE INVENTION

This invention relates to a method of preventing or reducing scarring of human skin.

The expression "scarring" used herein refers to abnormality in one or more of colour, contour (bulging/indentation), rugosity (roughness/smoothness) and texture (softness/hardness), arising during the human skin healing process. The expression "preventing" used herein in the context of scarring refers to an adjustment to the extent of development of scarring, whereby one or more of the colour, contour, rugosity and texture of the healed skin surface approximates on ordinary visual inspection to that of the patient's normal skin. The expression "reducing" used herein in the context of scarring refers to an adjustment to the extent of development of scarring, whereby one or more of the colour, contour, rugosity and texture of the healed skin surface approaches measurably closer to that of the patient's normal skin. The expression "skin" used herein includes all surface tissues of the human body and sub-surface structure thereat including mucosal membranes and eye tissue as well as ordinary skin. The expression "skin" includes a wound zone itself. The expression "wound" used herein refers to any skin lesion capable of triggering a healing process which may potentially lead to scarring, and includes wounds created by injury, wounds created by burning, wounds created by disease and wounds created by surgical procedures.

BACKGROUND OF THE INVENTION

When injury, disease or surgery disrupts the normal architecture of body tissues such as 5 the skin, eye and palmar aponeurosis of the hand, the body instigates a complex cascade of events collectively known as wound healing. These processes in the early human foetus lead to total regeneration of the damaged or destroyed tissue. However, in post natal humans, although the capacity of the outer layer of the skin, the epidermis, for regeneration is phenomenal, wound healing of the deeper skin layer, the dermis, is often accompanied by a fibroproliferative response that leads to the formation of a fibrotic scar. The tissues of the eye, particularly the cornea, often scar after surgery or trauma which reduces the vision of the individual. Dupuytren's disease affects the palmar aponeurosis of the hand. This condition is caused by scarring and fibrosis that causes contraction of the palmar structure, thus pulling the fingers permanently down towards the palm.

The severity of scarring of an individual in response to injury, disease or surgery is highly variable and depends on multiple factors, such as infection, wound extent and orientation. Nevertheless, even when all these factors are taken into account, the severity of so-called "normal" scarring still varies dramatically between individuals. This variation in the severity of scarring of the skin is perhaps most dramatically illustrated by the comparison of normal scars with pathological scarring conditions such as hypertrophic or keloid scarring.

Hypertrophic scars are characterised by extensive scar tissue, which contains an excess of collagen and is highly cellular (Rockwell et al., 1989. Plast. Recon. Surg. 84: 827-837, the disclosure of which is incorporated herein by reference). Redness, hypopigmentation or hyper-pigmentation of the affected area often accompanies these scars. Patients can also suffer from hyperaesthesia and pruritus and, in addition, contraction of scars located over a joint can lead to a loss of mobility. This distressing pathological condition can affect substantial numbers of patients who have suffered various types of skin trauma, with children under the age of four years particularly prone. Two of the latest estimates of the proportion of paediatric burns patients who suffer from this condition are as high as 44 and 60%.

At present there is no method of predicting which individuals will develop these scars, nor any method of preventing their formation or that of normal scars, nor any treatment. Effective therapies for both pathological scarring and normal scarring accordingly continue to be sought. It has been suggested for some time that insulin and its related growth factor family, insulin-like Growth Factors (hereinafter referred to as IGFs), may improve the rate of re-epithelialisation of wounds. U.S. Pat. Nos. 5,591,709 and 5,461,030 of Life Medical Sciences Inc (the disclosures of which are incorporated herein by reference) describe topically applied wound treatment formulations which are useful for treating wounds by accelerating wound healing. The formulations may, for example, contain insulin or IGF, together with further specified components. The formulations were tested on guinea-pigs for speed of wound healing, and it was observed in passing (see e.g. U.S. Pat. No. 5,591,709, column 23, line 46, to column 24, line 3) that a certain agarose gel based formulation produced a relatively soft, smooth, aesthetic and natural-looking scar in guinea-pig skin. However, no corresponding effect on the healing of human skin was reported, and the disclosure is unclear as to which specific hormone or hormone mixture was present in the agarose formulation for which the improved guinea-pig scar was noted. Although many groups (such as Pierre et al., 1998. J. Trauma. 44:34-345, the disclosure of which is incorporated herein by reference), have shown that systemic treatment with insulin and IGFs increases the speed of wound closure, the affect of these agents on human scar tissue formation has never before been investigated.

Peroxisome proliferator-activated receptors (PPARs) are known to control many cellular and metabolic processes and exist as three isotypes in vertebrates, PPARα, PPARβ/δ and PPARγ (Hanley et at, 1998 Journal of Investigative Dermatology, Vol. 110, pp. 368-375; Michalik et al., 2001, Journal of Cell Biology, Vol. 154, pp. 799-814). Each isoform displays differential tissue distribution in vertebrates, suggesting a specific role for each isoform. Both PPARα and PPARγ have been shown to play important roles in lipid homeostasis and inflammation. PPARα is important in skin development and wound healing, with PPARα ligands being able to accelerate fetal rat epidermal development. Although levels of PPARs reduce after birth, wounding or hair plucking may stimulate expression of these ligands. PPARγ agonists may mimic the effect of insulin. However, PPAR agonists have not hitherto been shown to have any anti-scarring activity when applied to human skin.

To date, with regard to the development of anti-scarring therapies, attention has been focussed on the finding that transforming growth factor beta 1 (TGFβ1) enhances scarring. Many groups have worked to develop ways of inhibiting TGFβ1, with some success. Methods used have included TGFβ1 receptor blocking antibodies or the application of mannose-6-phosphate, which prevents the activation of latent TGFβ1. The main problem with these approaches is that induction of scarring is not the only function of TGFβ1. TGFβ1 is known for its angiogenic properties. In addition, application of low doses of TGFβ1 is known to enhance re-epithelialisation of wounds. Thus, although the blocking of either the action or activation of TGFβ1 in incisional wounds may result in the reduction of scarring with relatively few deleterious side effects, the healing of larger wounds, which rely on epithelial migration for closure, may be delayed.

The initial induction of myofibroblasts, the concentration of which rises to a peak in the first few days of wound healing (the "pre-peak" phase) is thought to be due to the large amounts of growth factors such as TGFβ1 released early in the repair process. TGFβ1 is released in large quantities from the degranulating platelets within the forming clot, it is also secreted by multiple types of immune cells which migrate into the wound area and all of the major cell types participating in the repair process. TGFβ is linked with fibrosis in many different body tissues and is known to be a strong inducer of differentiation of fibroblasts into myofibroblasts in vitro. Thus, TGFβ is the most probable cause of the induction of the myofibroblast phenotype that occurs during wound repair.

BRIEF DESCRIPTION OF THE INVENTION

We have now surprisingly found that insulin, and not its highly related IGFs, prevents or reduces the formation of scar tissue in human skin whilst also improving the speed of re-epithelialisation of the wound in comparison with the speed of healing of an untreated comparable wound. It is effective in preventing or reducing scarring of all types of human skin wounds, such as for example incisional wounds and larger wounds.

Moreover, we have also surprisingly found that PPAR agonists exhibit similar activity.

We have found that the extent of formation of scar tissue in human skin is due to a complex in vivo mode of action in which the insulin or PPAR agonist predominantly inhibits the differentiation of myofibroblasts only after the peak concentration of myofibroblasts has been reached. This causes the myofibroblast concentration to fall off more rapidly after the peak in treated skin than in untreated skin. In addition, we have found that the strength of the resultant wound is not compromised by the relatively rapid loss of myofibroblasts in wounds treated according to the present invention.

According to a first aspect of the present invention, there is provided a method of reducing or preventing scarring in the skin of a human, which comprises administering to the skin an effective amount of an active agent selected from insulin and a peroxisome proliferator-activated receptor (PPAR) agonist.

The active agent as defined above may constitute the sole active agent used in the method. Alternatively, one active agent as defined above may be used in conjunction with the other active agent as defined above, with one or more other active agents known for wound care uses, or with any combination thereof.

The active agent is preferably applied as a composition comprising the active agent and one or more physiologically acceptable vehicle to act as a diluent, dispersant or carrier for the active agent. The composition may suitably be applied to the skin topically or by local injection.

The administration of the active agent is conducted before the peak myofibroblast level is reached in the wound tissue, preferably prior to or immediately after (e.g. up to about 2 to 5 days after) the wound is formed, ideally as soon as possible after formation of the wound.

The reduction or prevention of scarring according to the invention may suitably be accompanied by an acceleration of the rate of healing, in comparison with an untreated wound, to provide a dual-action wound treatment method which accelerates (or promotes) healing as well as reducing or preventing scarring.

The present invention accordingly provides a highly effective prophylactic and curative treatment for any individual suffering or likely to suffer tissue trauma, to reduce and/or prevent both normal and pathological scarring.

DETAILED DESCRIPTION OF THE INVENTION

Insulin

Insulin is a small (molecular weight approximately 6000) polypeptide hormone produced by the beta cells of the islets of Langerhans of the pancreas. It is made up of two chains of amino acids (designated A and B) which are held together by two disulphide bridges. Both chains are formed from the cleavage of a single helical chain known as pro-insulin, which consists of both the A and B chains of insulin connected by a peptide termed the C-peptide. Although the insulins of various species are highly homologous (differing only by a few amino acids) the sequence and number of amino acids making up the C-peptide can vary considerably. Under proper conditions, three dimers of insulin associate to form a hexamer of appropriate dihedral symmetry that is stabilised by the presence of two zinc ions. Insulin affects cell metabolism via receptors present on the cell surface.

The term "insulin" as used herein includes within its scope all insulin forms, and mixtures thereof. Suitable insulins are commercially available from Hoechst, Lilly, Novo Nordisk and CP Pharmaceuticals, for example.

Insulins that are suitable for the uses in accordance with the present invention can be sourced from a variety of different species due to the high degree of homology of insulin between species. Preferred insulins are those that are commonly available, including porcine, bovine or human insulins or mixtures thereof. The human insulins tend to be either derived by enzymatic modification and purification from porcine insulin or originate from microorganisms using standard recombinant DNA technology techniques. Insulins that are suitable for the uses in accordance with the present invention include conventional insulins, single-peak insulins, highly purified insulins, monocomponent insulins, purified insulins, human insulin (emp), semisynthetic insulins, human insulin (crb), human insulin (prb), human insulin (pyr) and biosynthetic human insulin. A wide variety of insulin forms are suitable for use in the present invention, for example, crystalline insulin, soluble insulin, neutral insulin, regular insulin and unmodified insulin, and formulations that prolong the duration of action of insulin such as suspensions formed by complexing insulin with a protein from which it is slowly released (examples are "protamine zinc insulin" and "isophane insulin") or by modifying the particle size (e.g., insulin zinc suspensions) or biphasic insulins which are mixtures providing both immediate and prolonged action.

Chemical modification of the insulin molecule has resulted in insulin forms such as delineated insulin (where the C-terminal alanine has been removed from the B chain of insulin), insulin defalan (where the terminal phenylalanine has been removed), sulphated insulin, insulin argine and insulin lispro. Such chemically modified insulins are also suitable and intended for the use in the present invention. Furthermore, insulins obtained by standard recombinant DNA technology are included within the scope of the present invention. Insulins obtained by standard recombinant DNA technology using nucleic acid chains that have a sequence identical to the naturally occurring gene encoding insulin in humans or other mammals are preferred. This nucleic acid sequence may be modified by either conservative base substitutions, such that it encodes the same amino acid sequence of naturally occurring insulin; or modified with base substitutions which encode a different amino acid sequence from that naturally occurring. Recombinant DNA technology has enabled production of other insulin analogues with altered pharmacokinetic profiles which are also included within the scope of the present invention.

The insulin to be employed in the uses according to the present invention is present in the pharmaceutical composition in an effective amount. Normally the total amount of the active is present in an amount between 50 picograms ($1.25 \times 10^{-6}$ IU) to 1000 micrograms (25 IU) per milliliter of the composition. More preferably the amount is 5 nanograms ($1.25 \times 10^{-4}$ IU) to 500 micrograms (12.5 IU) and most preferably from 50 nanograms ($1.25 \times 10^{-3}$ IU) to 50 micrograms (1.25 IU), in order to maximise benefits at minimum cost.

PPAR Agonist

PPAR agonists work by activating the peroxisome proliferator-activated receptor, an orphan nuclear DNA-binding steroid hormone receptor.

A list of examples of PPAR agonists suitable for use in the present invention is given in Tables 1 to 5 below. Any physiologically acceptable salt or other bioavailable form of these agonists may also be used. Where generic chemical names have been assigned to the agonists, these names are used. In some cases, however, agonists under pre-clinical or clinical trials are known only by commercial code numbers; in those cases the codes are used. In all cases, the names or codes used are established and widely recognized, and uniquely identify the agonists. The PPAR agonists used in the present invention may, for example, be specific to one or more PPAR isotype [e.g. the thiazolidinediones such as ciglitazone [(±)-5-[4-(1-methyl-cyclohexylmethoxy)-benzyl]-thiazolidine-2,4-dione] available from A.G. Scientific, Inc., San Diego, Calif. (www.agscientific.com; tel. +1 858 452 9925)] or may be a non-specific PPAR agonist [such as bezafibrate (2-[4-[2-[(4-chlorobenzoyl)-amino]ethyl]phenoxy]-2-methyl propanoic acid) (available from BIOMOL Research Laboratories, Inc., Plymouth Meeting, Pa.; www.biomol.com)]. Specific PPARγ agonists and dual PPARα/γ agonists from the thiazolidinedione family are preferred as PPAR agonist active agents in the present invention.

The PPAR agonist to be employed in the uses according to the present invention is present in the pharmaceutical composition in an effective amount. Normally the total amount of the active is present in a concentration between picomolar to 50 millimolar. Typical examples are given in Tables 1 to 5 below (key to compound classes: G=glitazones (thiazolidinediones), I=isoxazolidinediones, A=α-alkoxy-β-phenylpropanoic acids, F=fibrates, U=ureido-fibrates, T=tyrosine-based PPARγ agonists, D=2,3-disubstituted indole-5-acetic acid derivatives, P=phenylacetic acid derivatives, L=leukotriene antagonist, P=polyunsaturated fatty acids, E=eicosanoids such as the 15-lipoxygenase metabolites of polyunsaturated fatty acids, J=derivatives and metabolites of prostaglandins (particularly the J series):

TABLE 1

Synthetic PPARγ agonists

| Compounds | Published C50 (μM) | Compound class | Active range |
|---|---|---|---|
| Ciglitazone | 0.5-3 | G | 50 nM-50 μM |
| Troglitazone | 0.55 | G | 50 nM-50 μM |
| Pioglitazone | 0.58 | G | 50 nM-50 μM |
| Rosiglitazone | 0.043 | G | 5 nM-5 μM |
| GW 0207 | 0.044 | D | 5 nM-5 μM |
| GW 1929 | 0.0062 | T | 1 nM-1 μM |

TABLE 2

Other PPAR agonists which although not absolutely specific for the PPARγs act more strongly on these than PPARα or PPARβ/δ

| Compounds | Published C50 (μM) | Compound class | Active range |
|---|---|---|---|
| KRP-297 | 0.083 | G | 8 nM-8 μM |
| JTT-501 and its active metabolites | 0.083 | I | 8 nM-8 μM |
| SB213068 | 0.066 | A | 7 nM-7 μM |
| G1262570 | 0.00034 | T | 40 pM-40 nM |
| GW 7845 | 0.00071 | T | 70 pM-70 nM |

TABLE 3

Other general PPAR agonists

| Compounds | Published C50 (μM) | Compound class | Active range |
|---|---|---|---|
| L-796449 | 0.0052 | P | 500 pM-500 nM |
| L-165041 | 5.5 | L | 500 nM-500 μM |
| GW 9578 | 1.0 | U | 500 nM-500 μM |
| Bezafibrate | 60 | F | 6 nM-6 mM |

TABLE 4

Other compounds which act as strong agonists for PPAR receptors other than PPARγ and yet show weak action on the latter

| Compounds | Published C50 (μM) | Compound class | Active range |
|---|---|---|---|
| Wy-14643 | 60 | F | 6 μM-6 mM |
| Clofibrate and its active metabolites | ~500 | F | 50 μM-50 mM |
| Fenofibrate and its active metabolites | 300 | F | 30 μM-30 mM |
| GW 2433 | 2.5 | U | 300 nM-30 μM |

TABLE 5

Natural PPARγ agonists

| Compounds | Published C50 (μM) | Compound class | Active range |
|---|---|---|---|
| Linoleic acid | ~20 | P | 2 μM-2 mM |
| Linolenic acid | ~20 | P | 2 μM-2 mM |
| Arachidonic acid | ~20 | P | 2 μM-2 mM |
| Eicosapentaenoic acid (EPA) | ~20 | P | 2 μM-2 mM |
| 9-HODE | ~20 | E | 2 μM-2 mM |
| 13-HODE | ~20 | E | 2 μM-2 mM |
| 15-HETE | ~10 | E | 1 μM-1 mM |

TABLE 5-continued

Natural PPARγ agonists

| Compounds | Published C50 (μM) | Compound class | Active range |
|---|---|---|---|
| 15-deoxy-$\Delta^{12,14}$ prostaglandin $J_2$ | ~3 | J | 300 nM-300 μM |

\* 9-HODE = 9-hydroxy-10,12-octadecadienoic acid
13-HODE = 13-hydroxy-9,11-octadecadienoic acid
15-HETE = 15-hydroxy-eicosatetraenoic acid Composition Most preferably the composition or medicament in which the insulin or PPAR agonist is formulated for use according to the present invention is either a topical composition or an injectable composition for injecting locally, i.e. at or near to the site of the wound to be treated.

Topical or injectable compositions used according to the present invention suitably also comprise a pharmaceutically acceptable vehicle to act as a diluent, dispersant or carrier for the insulin or PPAR agonist. The vehicle may comprise materials commonly employed in wound treatment products such as water, saline solution, humectants, emulsifiers, solvents, and, for topical compositions, liquid or solid emollients, delivery polymers, silicone oils, thickeners, powders, propellants and the like.

Examples of such materials will be readily apparent to those skilled in this art, and need not be recited here. For example, as a humectant glycerol (glycerin) may be used.

The pH of the composition is preferably about neutral, e.g. in the range between about 6.0 to about 8.0. If necessary, the pH may be adjusted to the desired level using a strong acid or base, in conventional manner.

The vehicle will usually form from 0.1% to 99.9%, preferably 25% to 80%, by weight of the total composition and can, in the absence of other adjuncts, form the balance of the composition.

In a particularly preferred embodiment the topical composition comprises a delivery polymer that is saturated with the appropriate concentration of insulin or a PPAR agonist.

By "delivery polymers" is meant naturally occurring and/or synthetic polymers which facilitate the delivery of the active agent to its site of action. These polymers include hydrated or unhydrated hydrogels (e.g. hydroxyethylmethacrylate (HEMA), glycerolmethacrylate (GMA) and polyvinylpyrrolidone (PVP)); polyethylene glycol (PEG), methyl cellulose, agarose, extracellular matrix proteins such as collagens, fibronectins, fibrin, glycosaminoglycans, and mixtures thereof. In general, 0.1 to 50%, by weight of the composition, of delivery polymer is added to the insulin formulation to produce a gel.

As mentioned above, U.S. Pat. No. 5,591,709 and related publications deriving from the same inventor's work report an observation that a certain composition comprising agarose, the media specified in the Table in column 16 of U.S. Pat. No. 5,591,709, and water, appears to reduce or prevent scarring in guinea-pig skin. Although the prior art disclosure is not clear, it may be that the observation relates to a composition which contained as active agent insulin and one or more of: transferrin, triiodothyronine, thyroxine and human growth hormone. The reported observation is a passing comment in publications which are otherwise totally related to methods for accelerating and promoting wound healing. No attempt was made in the prior publications to predict an anti-scarring activity for insulin in human skin, and such a prediction would not have been credible on the basis of an isolated and unclearly reported observation in guinea-pig skin, in view of the substantial differences in the scarring mechanism between guinea-pig skin and human skin. For these reasons, the present invention is seen to be patentable. Nevertheless, we hereby reserve the right to disclaim any specific subject-matter of the present invention that may be found on proper examination according to law to be disclosed in an enabling manner by, or to be obvious from, such prior disclosures or any others. Without prejudice to our freedom of future action or argument, such a disclaimer, if and when entered in that event, may for example relate to the use of compositions which comprise agarose and, as active agent, insulin and optionally any one or combination of: transferrin, triiodothyronine, thyroxine and human growth hormone (all possible individualised agents from this list and all possible permutations of combinations of agents from this list being hereby deemed to be envisaged for the purposes of selection when formulating any possible future disclaimer).

It is preferred also that the composition for use in the present invention does not include IGF, which has been found to be insufficiently effective as an anti-scarring agent.

The composition for use in the present invention may most preferably consist essentially of the insulin or PPAR agonist or a mixture thereof, the delivery vehicle and optionally one or more further adjuncts conventionally used in compositions for medical or therapeutic use.

The composition for use in the present invention may, if desired, further comprise one or more additional active agents effective for reducing or preventing human skin scarring or for accelerating or enhancing the rate of human skin wound healing. Such additional active agent(s), when present, may be selected from such agents known in the art at the time. It will be well within the capability of a person skilled in the art to make such a selection and to select the appropriate effective dose of the active agent(s) used.

Optional Further Adjuncts

When present, the one or more optional further adjuncts are suitably selected from cell nutrients, sources of metal ions such as, for example, zinc and chromium ions (e.g. zinc oxide), anti-oxidants, antimicrobials, preservatives, opacifiers, colorants, perfumes, carrier proteins and buffers may be present in the composition. In the case of pharmaceutical compositions (medicaments), pharmaceutical grade materials should be used.

Such optional further adjunct(s), when present, may be selected from such adjuncts known in the art at the time. It will be well within the capability of a person skilled in the art to make such a selection and to select the appropriate amount of the adjunct(s) used.

Product Preparation, Form, Use and Packaging

To prepare the composition to be used in accordance with the present invention, the usual manner for preparing tissue treatment products may be employed. The active components and any other ingredients to be used are generally incorporated into a pharmaceutically acceptable vehicle in conventional manner. The active components can suitably first be dissolved or dispersed in a portion of the water or other solvent or liquid to be incorporated in the composition. The preferred dissolving or dispersing media for insulin and PPAR agonists are water or saline solutions.

The compositions may be in the form of conventional tissue treatment products such as cream, gel, lotions or solutions. The composition may be packaged in any suitable manner such as a jar, bottle, vial, tube or the like in a conventional manner.

The amount and frequency of application of the composition required for treatment will be readily apparent to one skilled in the art. In general, the treatment of a wound may be carried out by application, topically or by local injection, of a pharmaceutical composition comprising the insulin or PPAR agonist to the wound one or more times daily. Local injection is preferably made into the skin flanking the wound or the area requiring treatment. Typically, in solution or gel form, about 1 ml of formulation is applied per $cm^2$ of the tissue trauma depending on the depth and severity of the wound to be treated. The extent of prevention and/or reduction in scarring and enhanced re-epithelialisation of the tissue trauma will depend on the wound condition, the concentration of the active components, the amount of composition used and the frequency with which it is applied/injected.

The method of the present invention may be applied to the treatment of all types of human skin, including wound zones and eyes, where scarring is a possibility. More particularly, the present invention may be used to treat or prevent scarring of human skin resulting from burns, scalds, grazes, abrasions, cuts and other incisional wounds, surgery and pathological skin scarring conditions such as Dupuytren's disease, and specifically the conditions of fibrotic dermal scarring, hypertrophic scarring, keloid scarring and corneal and other ocular tissue scarring, which have hitherto been resistant to treatment.

Without wishing to be bound by theory, it is believed that insulin and PPAR agonists are effective at inhibiting myofibroblast differentiation in the process of human skin healing, and that the inhibition of myofibroblast differentiation is a marker for efficacy in reducing or preventing scarring in a range of wound types. Generally speaking, myofibroblasts become differentiated from other cells in the wound within a few days after the onset of healing, and in the rat model can reach a peak where about 70% of the fibroblastic cells present are of the myofibroblast phenotype. The phase of wound healing in which the levels of differentiated myofibroblast cells in the wound tissue are increasing to a peak (maximum) is referred to herein as the "pre-peak" phase, and typically lasts for a few days, e.g. up to about one to two weeks, although the length of time varies between individual cases. After this time (i.e., during the "post-peak" phase, which may typically last for a further 20 to 25 days), the number of myofibroblasts present in the forming scar tissue begins to reduce via apoptosis, until by about 30 days no myofibroblasts are obvious within the scar. It is believed that the present invention works by accelerating the post-peak decline in the concentration of myofibroblasts without substantially affecting the pre-peak increase.

BRIEF DESCRIPTION OF THE DRAWINGS

The present invention will now be described in more detail, but without limitation and purely for illustration, with reference to the accompanying drawings and the following Examples. In the drawings.

EXAMPLES AND DETAILED DESCRIPTION OF THE DRAWINGS

Example 1

In Vitro Study

One of the most important cell types in both normal and pathological scar formation is the myofibroblast. These cells, which differentiate from the unwounded tissue cell type (fibroblasts), are responsible for laying down scar tissue. Indeed myofibroblasts remain present in hypertrophic scars up to four years after the original wounding event. An in vitro assay was accordingly developed to identify actives which prevent or reduce myofibroblast formation and thus identify actives which are effective in reducing and/or preventing scar tissue formation.

Assay

Fibroblast cultures were initiated from normal skin, normal scars, hypertrophic scars (HTS) and burns scars.

Each culture was split into seven parts (A to G) and grown in the following different growth media:

(A) was grown in normal growth medium (hereinafter referred to as NGM) which consisted of Dulbecco's modified Eagles Medium (DMEM) plus 10% Foetal Calf Serum (FCS);

(B) was grown in growth factor depleted medium (hereinafter referred to as GF depleted) which is NGM that is depleted of active polypeptide growth factors including TGFP. It is prepared by treating FCS with a reducing agent in order to attack and cleave the disulphide bonds that determine the conformation and thus the biological activity of the polypeptide growth factors;

(C) ($C_1$-$C_3$) were grown in growth factor depleted medium plus 10 ng/ml-5 µg/ml of insulin (hereinafter referred to as GF depleted+I);

(D) ($D_1$-$D_4$) were grown in growth factor depleted medium plus 1 ng/ml-100 ng/ml of insulin-like Growth Factor-I) (IGF-I) (hereinafter referred to as GF depleted+IGF-I); (E) ($E_1$-$E_3$) were grown in growth factor depleted medium plus 50 ng/ml-200 mg/ml of insulin-like Growth Factor II (IGF-II) (hereinafter referred to as GF depleted+IGFII); (F) ($F_1F_3$) were grown in growth factor depleted medium plus 25 ng/ml to 100 ng/ml of basic fibroblast growth factor (bFGF) (hereinafter referred to as GF depleted and bFGF);

(G) (G1-G3) were grown in growth factor depleted medium plus 25 ng/ml to 100 ng/ml of platelet derived growth factor (PDGF) (hereinafter referred to as GF depleted+PDGF).

The fibroblasts were grown in these media (which was replenished twice weekly) for fourteen days, fixed and stained immunohistochemically using an antibody specific for α-smooth muscle actin (a marker of myofibroblasts). The stain caused α-smooth muscle actin to fluoresce green and accordingly cells that had stained green were identified as myofibroblasts. The number of these was counted, as was the total number of cells present, and the proportion of myofibroblasts was then calculated. In this manner, the number of myofibroblasts present in each culture was determined as a percentage of the total number of cells in the culture population.

Results

TABLE 6

| MEDIUM | Normal Skin | Normal Scar | HTS | Burns Scar |
|---|---|---|---|---|
| | NUMBER OF MYOFIBROBLASTS-PERCENTAGE OF TOTAL CELL POPULATION | | | |
| A-NGM | 7.58 | 4.59 | 4.27 | 13.33 |
| B-GF DEPLETED | 19.15 | 34.71 | 35.14 | 42.55 |
| $C_1$-GF DEPLETED + 10 ng/ml INSULIN | | | | 16.44 |
| $C_2$-GF DEPLETED + 100 ng/ml INSULIN | | | | 15.91 |
| $C_3$-GF DEPLETED + 5 μg/ml INSULIN | 5.26 | 6.14 | 3.23 | 8.20 |
| $D_1$-GF DEPLETED + 1 ng/ml IGF-I | | | | 40.79 |
| $D_2$-GF DEPLETED + 10 ng/ml IGF-I | | | | 43.90 |
| $D_3$-GF DEPLETED + 50 ng/ml IGF-I | | | | 51.51 |
| $D_4$-GF DEPLETED + 100 ng/ml IGF-I | | | | 47.00 |
| E1-GF DEPLETED MEDIUM + 50 ng/ml IGF-II | | | | 37.93 |
| E2-GF DEPLETED MEDIUM + 100 ng/ml IGF-II | | | | 40.26 |
| E3-GF DEPLETED MEDIUM + 200 ng/ml IGF-II | | | | 38.52 |
| F1-GF DEPLETED MEDIUM + 25 ng/ml bFGF | | | | 31.82 |
| F2-GF DEPLETED MEDIUM + 100 ng/ml bFGF | | | | 34.21 |
| G1-GF DEPLETED MEDIUM + 25 ng/ml PDGF | | | | 50.95 |
| G2-GF DEPLETED MEDIUM + 50 ng/ml PDGF | | | | 52.84 |
| G3-GF DEPLETED MEDIUM + 100 ng/ml PDGF | | | | 53.35 |

CONCLUSIONS

A small but significant number of myofibroblasts are present in the NGM only cultures (see (A)). This phenomenon is thought to be due to the presence of TGFβ in the FCS which makes up the medium, which is known to induce fibroblasts to differentiate into myofibroblasts whether they be derived from normal skin, normal scars or pathological scars.

A surprisingly large number of myofibroblasts are present in the GF depleted cultures (see (B)). It was expected that because TGFβ was thought responsible for the presence of the myofibroblasts in NGM cultures, then the culture of fibroblasts in GF depleted medium should reduce the number of myofibroblasts seen in the population. However, contrary to expectation, no matter what the source of fibroblasts, culture in GF depleted medium promoted fibroblast differentiation into myofibroblasts. This surprising result suggests that FCS contains actives that inhibit myofibroblast formation, with the biological activity of those actives being strictly dependant on the presence of intact disulphide bonds.

During attempts to identify the polypeptide constituent of FCS that was responsible for inhibition of myofibroblast differentiation, it was discovered that insulin but not its related factors IGF-I and IGF-II nor bFGF or PDGF were capable of inhibiting myofibroblast differentiation. (Compare C with D to G Table 6). All the growth factors were titrated over their respective biofunctional ranges (insulin: 10 ng/ml-5 m/ml, IGF-I: 1-100 ng/ml IGF-II: 50 ng/ml-200 ng/ml, bFGF: 25 ng/ml-100 ng/ml, PDGF: 25 ng/ml-100 ng/ml). All of these factors are known to be present in serum and their biological activities are strictly dependent on the presence of intact disulphide bonds.

Comparing B and C it can be seen that the addition of exogenous insulin specifically to fibroblasts cultured in GF depleted medium completely abrogates the induction of myofibroblast differentiation seen in this medium. Importantly, and further surprisingly, comparing the data in C and D for burns scar cells, it can be seen from the data presented in C that insulin is equally effective at inhibiting myofibroblasts differentiation for both normal skin, normal scar and pathological cells and thus is suitable both for preventing scar formation and reducing the extent of scarring in both normal wound healing and pathological scarring conditions. Further surprisingly, the related IGFs do not exhibit this technical effect thus demonstrating that the effect is insulin specific.

This finding, that the single specific growth factor insulin can prevent or at least reduce the formation of myofibroblasts, has wide implications in the fields of both cutaneous scarring and fibrosis generally. This new use of insulin as a treatment for preventing and/or reducing scar tissue formation is accordingly an important medical advancement for tissue trauma sufferers. This new use is particularly beneficial as insulin also promotes the positive events of the wound healing process such as enhancing the re-epithelialisation of wounds and thus a dual action treatment for wounds is accordingly provided for the first time.

Example 2

In Vivo Study

The efficacy of an exemplifying treatment protocol using insulin in vivo was determined using a murine incisional wound healing model in the manner described below.

After general anaesthesia, both posterior flanks on male BALB/c mice were shaved and cleaned with chlorhexidine in spirit. Two 1.5 cm wounds were marked (one in each flank) parallel to the spine with permanent marker. Full thickness incisions were made along these marks down to the level of the chest wall. Both lateral skin flaps were dissected from the underlying chest wall and the wound assessed from haemorrhage. The wound edges were then infiltrated with test substance or vehicle only control, as appropriate, by injection into the wound edges. Insulatard® was diluted in normal saline (0.9%) to give a final test solution of 1 IU/ml. 0.15 ml of this test solution (0.15 IU) was applied to one of the test wounds and saline alone was applied to the contralateral wound on the same animal. Wounds were closed with interrupted 5/0 Prolene® suture. Mice were recovered from the anaesthetic individually and housed in groups of 4. Wound healing was allowed to progress for 14 days (the time at which myofibroblast proportions are usually maximal in vitro), the mice were sacrificed and the wound area harvested for standard paraffin wax embedding and sectioning.

The wounds were analysed in the following manner: The comparison of the actual severity of scarring is impossible in this and all other animal models, since in contrast to human wounds, animal wounds are rapidly closed by way of swift epidermal contraction leaving minimal areas of scarring in any case. We therefore attempted to judge the efficacy of insulin in vivo on its ability to affect the number of myofibroblasts present using immunohistochemical staining methods for the myofibroblast marker, α smooth muscle actin. To allow semi-quantitative analysis of the resulting staining, a visual grading system was developed. Scars were assessed and allocated a score depending on the intensity of alpha smooth muscle actin staining within each section. The intensity of staining varied from absent to strong and a numerical score was allocated to each staining intensity (i.e. 0 for absent staining, 1 for weak, 2 for moderate and 3 for strong). Each scar was assessed at a number (minimum of 3) points along its length and the intensity was scored and averaged for each section to allow comparisons between treatments. Two independent assessors assessed the scoring blindly. The number of wounds assessed for each experimental group was 8. The results and statistical analysis are set out in Table 7 below:

TABLE 7

| | Mean score of α-smooth muscle actin staining (out of maximum of 3) | Standard deviation | P Value (T Test) |
|---|---|---|---|
| Insulin | 0.486 | 0.249 | |
| Saline only | 1.25 | 0.447 | 0.004 |

It can be seen from the data as presented in Table 7 that insulin is capable of significantly inhibiting myofibroblast differentiation in vivo.

Example 3

The following injectable composition was prepared in conventional manner. It was found both to prevent and reduce scar tissue formation when locally injected into wounds in accordance with the present invention. The formulation is also suitable for topical application.

Each milliliter of the formulation contains:

100 IU of insulin (human insulin (pyr) which is of recombinant origin produced in yeast), 3.78 mg dibasic sodium phosphate, 1.76 mg m-cresol, 0.715 mg phenol, zinc oxide, (content adjusted to provide 0.025 mg zinc ion), 0.28 mg protamine sulphate, 16 mg glycerin, and water to dilute to the required concentrations. The pH range of the composition is preferably 7.0-7.8, but 10% sodium hydroxide or hydrochloric acid may be used to adjust the pH, as required.

Example 4

Does Myofibroblast Differentiation in GF Depleted Medium (Example 1) Occur Via Autocrine Action of TGFβ?

In a rat model of wound healing, differentiated myofibroblasts become obvious within the wound at approximately 6 days post wounding (although actual onset of differentiation must begin earlier) and their numbers gradually increase, reaching a peak where approximately 70% of the fibroblastic cells present are of the myofibroblast phenotype. After this time the number of cells, particularly myofibroblasts, present in the forming scar tissue begins to reduce via apoptosis, until at 30 days no myofibroblasts are obvious within the scar.

However, the in vitro studies reported in Example 1 above differ considerably from the situation in vivo, being greatly simplified and thus more defined. Two observations which are of particular note are that the only cell type present in vitro is the fibroblast and the GF depleted (GFD) media is depleted of TGFβ activity. Yet even so, differentiation of fibroblasts into myofibroblasts still takes place in the absence of inhibitory factors in serum (GFD medium, Example 1, medium B). Since it is known that TGFβ is undetectable in fresh GFD medium, it is likely that the induction of myofibroblast differentiation seen in this in vitro system is due to autocrine secretion of TGFβ by the dermal fibroblasts themselves. To examine this possibility the sugar mannose-6-phosphate (M-6-P) was used. This sugar binds to the M-6-P/IGF-II receptor, which is required for the activation of the inactive pro-form of secreted TGFβ1, and is known to block activation of TGFβ.

Method

Fibroblast cultures were initiated from normal scars (NS) and hypertrophic scars (HTS). Each culture was seeded onto coverslips in 6-well plates and triplicate coverslips were treated with one of six different media for 13 days (media replaced twice weekly), after which they were harvested for staining for α-smooth muscle actin (as in Example 1 above). The media groups consisted of NGM, GFD, GFD plus 5 μg/ml insulin (I), GFD plus 5 μg/ml insulin plus 100 μM M-6-P (I+M6P), GFD plus 100 μM M-6-P (100 M6P), and finally GFD plus 10 μM M-6-P (10 M6P). The number of myofibroblasts was calculated as a percentage of the total cell population and the results are shown in FIGS. 1 and 2 of the drawings.

Results and Discussion

Figure 1:
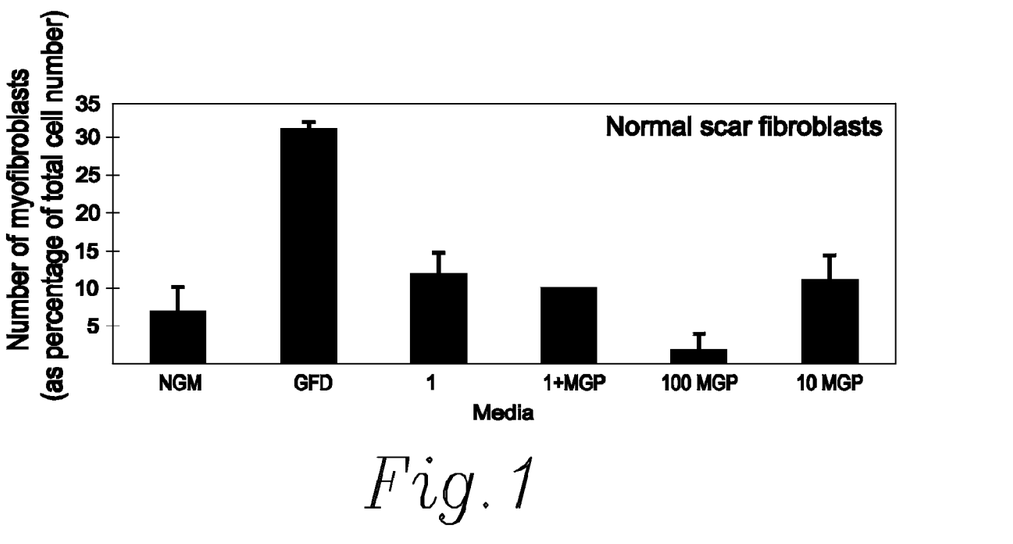
FIG. 1 shows the number of myofibroblasts as a percentage of total cell number in fibroblast cultures obtained using human normal scar tissue cultured for 13 days in the different media described in Example 4 below.
Figure 2:
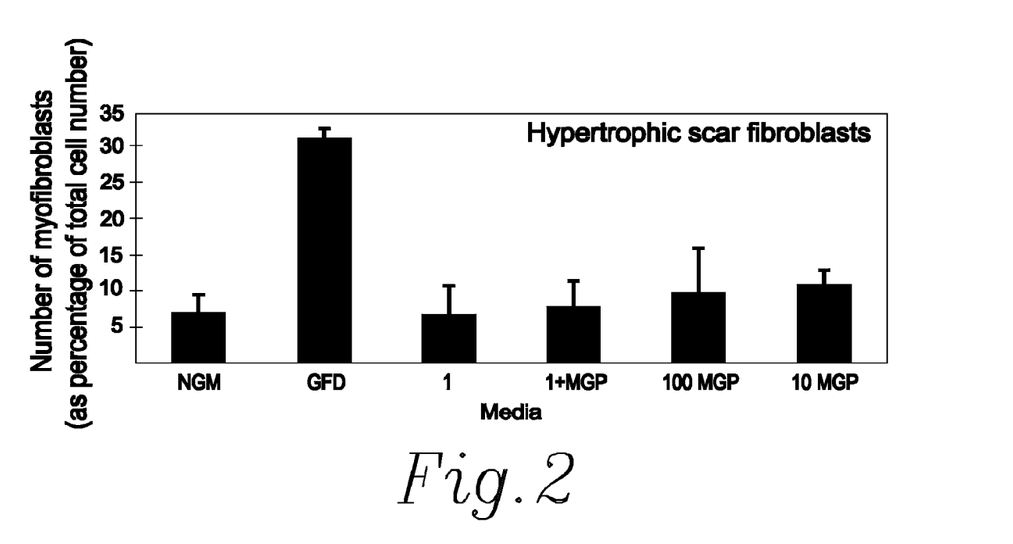
FIG. 2 shows the number of myofibroblasts as a percentage of total cell number in fibroblast cultures obtained using human hypertrophic scar tissue cultured for 13 days in the different media described in Example 4 below.

As can be seen from FIGS. 1 and 2, mannose-6-phosphate inhibits the induction of myofibroblast differentiation seen in GFD medium in fibroblast cultures from both normal and hypertrophic scars, but its effect is not synergistic with that of the optimum dose of insulin.

It would therefore seem that the induction of myofibroblast differentiation seen to occur in GFD medium is due to the autocrine secretion and local activation of TGFβ. Furthermore, it would appear that insulin prevents the "end result" (myofibroblast differentiation) of the autocrine action of TGFβ in some way.

Example 5

Does Insulin Affect the Action of Active Exogenous TGFβ on Fibroblast Differentiation?

It is possible that insulin either (i) acts directly on the ability of fibroblasts to differentiate into myofibroblasts per se or on specific characteristics of that transition/phenotype, such as expression of the α-smooth muscle actin protein, or (ii) acts indirectly via the TGFβ mechanism of inducing myofibroblasts. This Example investigates which hypothesis seems the more feasible.

Method

Fibroblasts cultures were initiated from normal and hypertrophic scars. The cells were then seeded onto coverslips in four different types of medium: NGM, NGM plus 5 µg/ml Insulin (optimal concentration for inhibition of myofibroblast differentiation) [NGM+I], NGM plus 0.5 ng/ml of TGFβ1 (just sub optimal for induction of myofibroblasts differentiation) [NGM+TGF], and NGM plus 5 µg/ml insulin plus 0.5 ng/ml TGFβ1 [TGF+I]. The cells were cultured for 5 days in these media and then harvested for staining for α-smooth muscle actin. The number of myofibroblasts were counted and calculated as a percentage of the total cells present. The results are given in FIG. 3 of the drawings.

Results and Discussion

Figure 3:
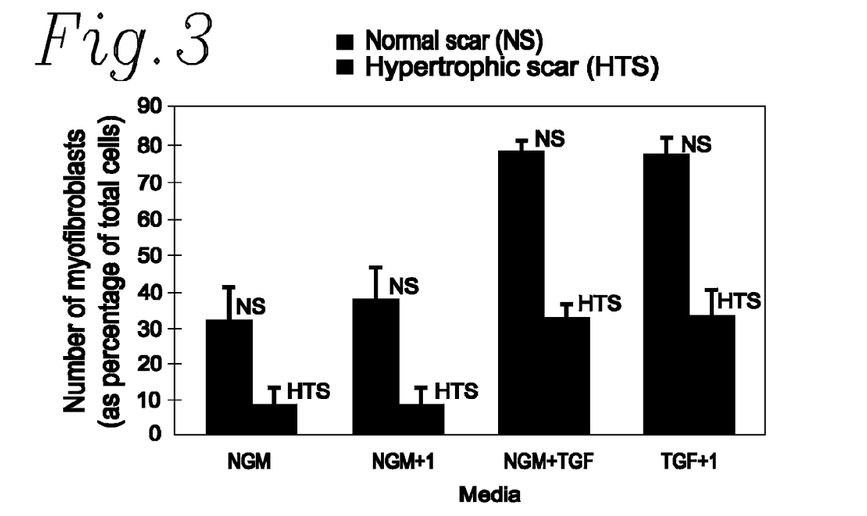
FIG. 3 shows the number of myofibroblasts as a percentage of total cell number in fibroblast cultures obtained using both human normal and hypertrophic scar tissue cultured for 5 days in the different media described in Example 5 below.

As can be seen in FIG. 3, the addition of even sub-optimal levels of TGFβ1 to fibroblast cultures induces a rapid (within 5 days) induction of myofibroblast differentiation in a significant number of cells present in fibroblast cultures derived from both normal and hypertrophic scars. In addition it is clear that addition of optimal levels of insulin has no effect on the rapid induction of myofibroblast differentiation by active TGFβ1. These results suggest that insulin treatment of cells over this time period does not affect the cells' ability to differentiate into myofibroblasts given the correct active stimulus.

Example 6

Comparison of the Time Courses of Myofibroblast Induction

It is possible that insulin either acts on the induction of differentiation by autocrine TGFβ (apparently requiring local activation by the fibroblasts) or acts directly on myofibroblast induction in some way, but only after long term (14 day) treatment (unlikely due to the efficacy of a single dose of insulin in vivo, Example 2) or after a certain period of time has elapsed since treatment (14 days). If the interpretation of these results is correct, then insulin treatment in vivo should not affect the initial ("pre-peak") rapid induction of myofibroblasts that is in response to the massive release of TGFβ into the wound area but should affect a more sustained ("post-peak") induction of myofibroblasts that is due to either prolonged release of TGFβ within the forming scar or specifically autocrine action of TGEβ on the dermal fibroblasts themselves.

To examine this possibility, this Example shows a time course of α-smooth muscle actin expression in vivo, with and without insulin treatment, in comparison with the timing of its expression in the in vitro model of GFD medium.

In Vivo Study

To determine insulin's effect on the time course of myofibroblast formation and clearance from the wound, an incisional wound healing time course was undertaken over a 28-day period.

Method

Briefly the incisional model was initiated as described previously, with two 1.5 cm full thickness incisional wounds created on the posterior flanks of 48 male BALB/c mice after anaesthesia. One wound per mouse was selected for treatment with a single dose administration of 0.15 ml insulin given on day 0 (Insulatard 0.15 IU), with equal numbers of left and right wounds treated. The remaining wounds received 0.15 ml saline as vehicle control, administered at the same time point. Both substances were administered as a local infiltration of the wound edges as described in Example 2 above.

Figure 4:
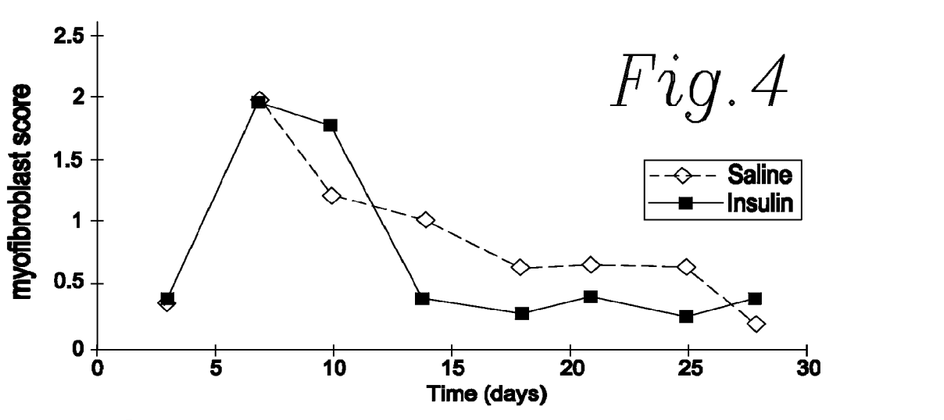
FIG. 4 shows the change in presence of myofibroblasts in mouse skin over a period of 28 days post wounding, under wound treatment with insulin, using saline as a control (see Example 6 for detail)

The mice were culled at the following times after wounding: 3, 7, 10, 14, 17, 21, 24 and 28 days, and their tissue processed for immunohistochemical analysis to determine myofibroblast number. Incisional wounds (4 per treatment group) were stained for α-smooth muscle actin and scored at a minimum of 3 random points along their length using the scoring system outlined in Example 2 above. The mean myofibroblast scores for each time point are shown in FIG. 4 of the drawings. In the figure, error bars have been omitted for clarity.

Results and Discussion

Myofibroblast scores for all wounds increased over the first 7 days following injury to reach a maximum of 1.96 (saline treatment group) and 1.92 (insulin treatment). Thereafter, the shape of the plots differs; with the myofibroblast scores falling gradually in the saline treatment group approximately over a 10 day period (up until day 17), reaching a plateau of a slightly higher than normal score which persists over the next approximately 8 days (day 25) and only drops down to normal levels on day 30. However, in those wounds treated with insulin, although the initial decrease in myofibroblast score seen between day 7 and 10 is less than that seen in the saline alone group (possibly due to insulin's anti-apoptotic effect), the decrease seen after day 10 is rapid and dramatic, with the myofibroblast score dropping down to normal immediately by the next time point of day 14.

It would seem from the above results that, in the absence of insulin treatment, there is an initial rapid induction of differentiation into myofibroblasts followed by a slower or more prolonged second stage, evident as the shoulder of the curve from 10 days. The level of myofibroblasts is then sustained up until approximately 14 days, after which it slowly drops. Insulin treatment, whilst not reducing—and in fact slightly prolonging—the presence of myofibroblasts produced by the initial phase of differentiation, rapidly reduces the apparent second phase of myofibroblast induction.

Example 7

For comparison of the in vitro induction of myofibroblasts with the timing of each in vivo phase, the following experiment was conducted.

In Vitro Study
Method

Fibroblast cell lines initiated from normal skin dermis were used for experimentation. Early passage (less than p3) cells were seeded onto coverslips in 6-well plates in either NGM (10% normal FCS) or GFD medium (made up as detailed above). For each media, triplicate wells were set up for a number of time points as follows: 3, 6, 9, 13, 16, and 20 days. The cells were then cultured with media refreshed twice weekly and the coverslips were harvested for staining at the requisite time points. Staining and quantification of cells expressing α-smooth muscle actin was performed as in Example 1 above. The results are shown in FIG. 5 of the drawings.

Results and Discussion

Figure 5:
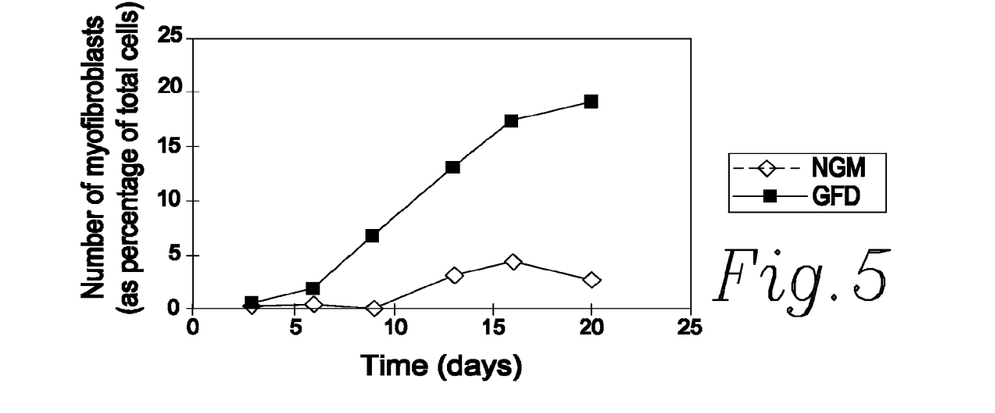
FIG. 5 shows the time-dependent changes in the number of myofibroblasts as a percentage of total cell number grown in fibroblast cell lines initiated from normal human skin tissue over 20 days in the different media described in Example 7 below.

FIG. 5 shows that the proportion of myofibroblasts begins to increase approximately 6 days after the experiment was initiated, and that this increases gradually over the following 10 days reaching a peak at approximately day 16, when a maximum of only 20% of the total cells present are of the myofibroblast phenotype. This time course of myofibroblast induction, which is known to be due to autocrine action of TGFβ, is more in accordance with the second phase of myofibroblast differentiation described in the in vivo study. Moreover, the in vitro induction and the second phase in vivo induction are both able to be inhibited by insulin.

These results are consistent with the hypothesis that insulin treatment only reduces prolonged induction of myofibroblasts seen during wound healing, which is exactly the phase that is probably excessive during the formation of pathologically excessive scars such as hypertrophic scars and keloids.

Example 8

Does Insulin Treatment Affect the Breaking Strength of the Healed Wound?

Method

To assess the effect administration of insulin may have on wound breaking strength, incisional wounds created in the murine model (as in Example 2 above) that had been treated with single doses of insulin or saline (at Day 0) or 4 doses of insulin (at Days 0, 3, 7 and 10) were harvested after 14 days (n=4 for each group) and the wound breaking stress assessed using tensiometry. Scars were wrapped in saline soaked swabs and transported immediately to the laboratory for testing. Each scar was dissected into 2 equal strips (perpendicular to the line of the scar), each of which was measured using a Nikon Shadowmeter. The strip of tissue was mounted on the tensiometer, with the scar mounted at 6 mm from the jaws of the clamps. Traction was applied across the scar at a constant rate of 10 mm/minute, and the force required for disruption of the scar measured. Stress values were calculated by normalising load values to cross-sectional area of each specimen and are given in units of MPa.

Results and Discussion

Figure 6:
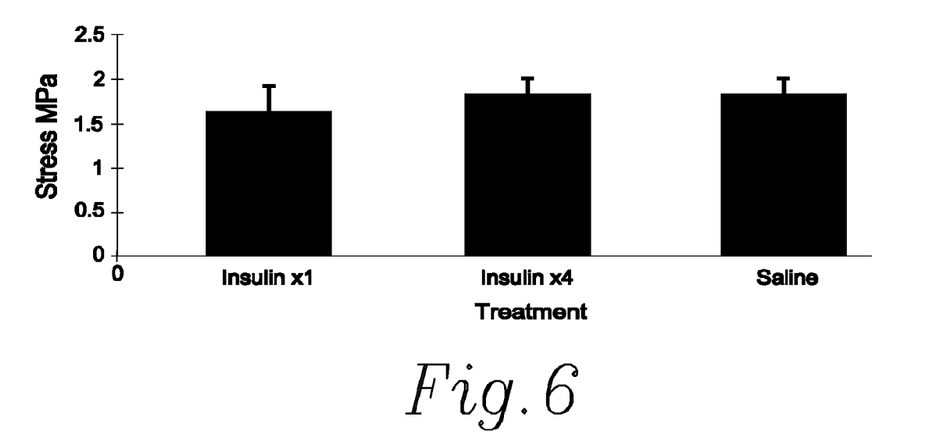
FIG. 6 shows median and standard deviation for the stress (in MPa) required to disrupt murine incisional scars previously treated with single or multiple dose administrations of insulin or saline (control) (see Example 8 for detail)

Each of the samples tested disrupted through the line of the scar. FIG. 6 shows both the mean and standard deviation for each group of scars. Saline-treated incisional wounds exhibited a median wound breaking strength of 1.71 MPa (±0.29). Treatment of the wounds with either 1 dose or 4 doses of insulin resulted in median wound breaking strengths of 1.62 MPa (±0.31) and 1.80 MPa (±0.19) respectively, which were not significantly different to the control.

The results suggest that insulin treatment of wounds in this way does not significantly change the strength of the wound and may therefore be used in humans without concern for the resulting wound strength.

Example 9

Tests Using PPAR Agonists

Method

Figure 7:
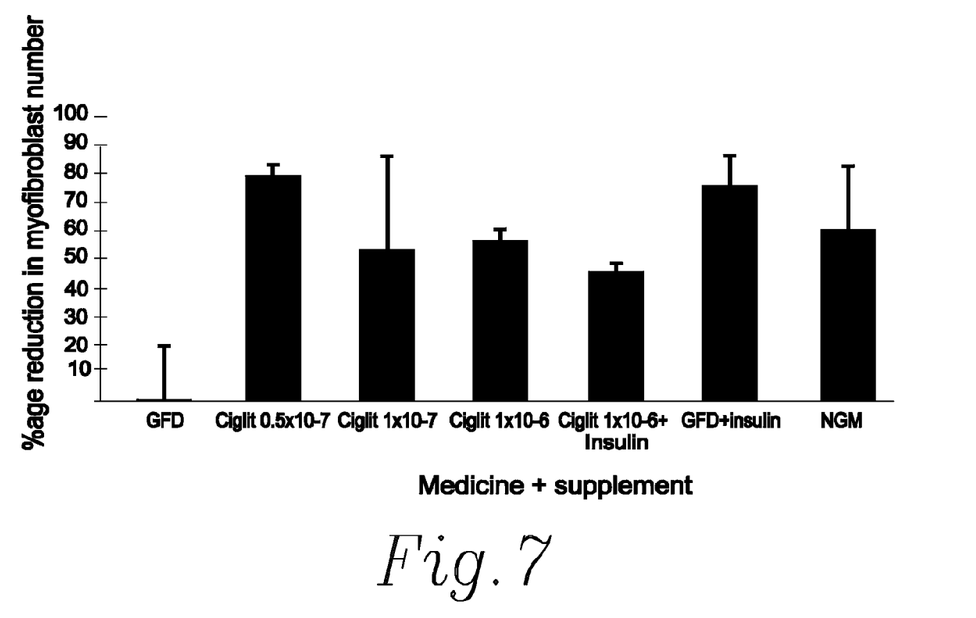
FIG. 7 shows the mean percentage reduction in myofibroblast number in human dermal fibroblast cell lines over 14 days, under treatment with PPAR agonist containing media in comparison with the control media stated in Example 9.

Dermal fibroblast cell lines were derived from 3 patients and seeded individually onto sterile coverslips. Each cell line was tested in triplicate for each of the following media: NGM, GFD, GFD supplemented with $0.5 \times 10^{-7}$M, $10^{-7}$M, or $10^{-6}$M ciglitazone alone, $10^{-6}$M ciglitazone plus 11 U/ml insulin (Insulatard) or 11 U/ml insulin alone. Medium was refreshed twice weekly and cultures were harvested for immunohistochemical staining for α-smooth muscle actin after 14 days. The number of myofibroblasts was counted and calculated as a percentage of the total cells present, and since the ability of each cell line to differentiate into myofibroblasts varied extensively, the results were normalised as follows. Results are expressed as the mean percentage reduction in myofibroblast number for each treatment as compared to the proportion of myofibroblasts identified in GFD medium alone for that cell line. The results are shown in FIG. 7 of the drawings. The error bars represent plus or minus one standard deviation.

Results and Discussion

Addition of ciglitazone to fibroblasts cultured in growth factor depleted medium in vitro significantly reduces the numbers of myofibroblasts ($P<0.05$) present in dermal fibroblast cultures (when compared to the same fibroblasts cultured in GFD Medium) by 57% (±4.5) when added at a concentration of $10^{-6}$M. Similar significant reductions of 53% (±33.1) can be observed if this compound is used at a concentration of $10^{-7}$M. Further reducing the concentration of ciglitazone again to $0.5 \times 10^{-7}$M significantly reduces myofibroblast numbers by 79% (±3.3). However, adding both insulin and ciglitazone at optimal concentrations reduces myofibroblast numbers by only 46.6% (±2.7), whereas addition of insulin alone results in a 76.6% (±10.6) reduction in myofibroblast numbers. The action of insulin and ciglitazone is therefore not synergistic.

It is clear that ciglitazone across the whole range tested shows an ability to inhibit the formation of myofibroblasts that normally occurs in GFD medium and that has been ascribed to the autocrine action of TGFβ. These results suggest a potential role for the PPARs in wound healing and scar formation and show that their agonists should be of use in the prevention/reduction of myofibroblast differentiation and hence the prophylaxis or reduction of scarring. Recent work (Hanley et al., 1998 Journal of Investigative Dermatology, Vol. 110, pp. 368-375; Michalik et al., 2001, Journal of Cell Biology, Vol. 154, pp. 799-814) has suggested that PPAR expression and ligand modulation within the skin may show potential for improving poor wound closure. PPARγ agonists are thought to be capable of rerouting the differentiation sequence by altering the expression of specific genes in immature cells. Indeed, troglitazone has been shown to reduce α-smooth muscle actin expression in myoblasts after 5 days. In addition, 5 day treatment with troglitazone was shown to potentiate the effect of insulin on an important component of its signalling pathway, IRS-1 dependent PI-3 kinase activity.

Interestingly, use of non-specific PPAR agonists, such as LY171883 increase the numbers of myofibroblasts. It is therefore possible that the activation of other PPAR ligands (PPARα or PPARδ) may actually cause myofibroblast differentiation.

The above broadly describes the present invention, without limitation. Variations and modifications as will be readily apparent to those of ordinary skill in this art are intended to be within the scope of the present application and any subsequent patent(s).

What is claimed is:

1. A method of reducing dermal scarring of a skin wound of a human caused by incisions, abrasions, grazes, and cuts when such dermal scarring is compared with untreated skin, the method comprising:
   administering to the skin wound a composition consisting of an effective amount of insulin dissolved in a pharmaceutically acceptable liquid vehicle, wherein the composition is injected as a single injectable dose up to 2 days after the skin wound is formed.

2. The method according to claim 1, wherein insulin is administered to the vicinity of the skin wound.

3. The method according to claim 1, wherein the pharmaceutically acceptable liquid vehicle comprises a solution that includes one or more of water, saline solutions, humectants, emulsifiers, or solvents.

4. The method according to claim 1, wherein the effective amount comprises a concentration of insulin of $1.25 \times 10^{-6}$ IU to 25 IU per millimeter.

5. A method of reducing dermal scarring of a skin wound of a human compared with untreated skin, the method comprising:
   administering a composition to a vicinity of the skin wound, the composition consisting of an effective amount of insulin dissolved in a pharmaceutically acceptable diluent, wherein the composition is administered as a single injectable dose up to 2 days after the skin wound is formed.

6. The method according to claim 5, wherein the composition is administered with one or more other active agents known for wound care uses.

7. The method according to claim 5, wherein the scarring is selected from grazes, abrasions, incisions, and cuts.

8. The method according to claim 5, wherein the effective amount comprises a concentration of insulin of $1.25 \times 10^{-6}$ IU to 25 IU per millimeter.

9. The method according to claim 4, wherein the pharmaceutically acceptable diluent comprises a solution that includes one or more of water, saline solutions, humectants, emulsifiers, or solvents.

* * * * *